United States Patent [19]

Kitano et al.

[11] Patent Number: 4,656,131

[45] Date of Patent: Apr. 7, 1987

[54] METHOD FOR PRODUCING INTERFERONS

[75] Inventors: Kazuaki Kitano, Sakai; Fujimoto Shigeru, Ikeda, both of Japan

[73] Assignee: Takeda Chemical Industries, Ltd., Osaka, Japan

[21] Appl. No.: 674,598

[22] Filed: Nov. 26, 1984

[30] Foreign Application Priority Data

Nov. 30, 1983 [JP] Japan ................................ 58-227750

[51] Int. Cl.$^4$ .............................................. C12P 21/00
[52] U.S. Cl. ........................................ 435/68; 424/85
[58] Field of Search .............. 435/68, 253, 811, 172.3; 424/85

[56] References Cited

U.S. PATENT DOCUMENTS 4,518,584  5/1985  Mark et al. ........................... 435/253

FOREIGN PATENT DOCUMENTS 0181224  10/1984  Japan .

OTHER PUBLICATIONS

Goeddel et al., Nature, vol. 287, pp. 411–416, 1980.

*Primary Examiner*—Blondel Hazel
*Attorney, Agent, or Firm*—David G. Conlin; Ronald I. Eisenstein

[57] ABSTRACT

A method for producing high yields of interferons which comprises cultivating a microorganism carrying an expression vector with a structural gene of interferon inserted therein in a chemically defined medium containing L-glutamic acid and an iron ion source and preferably further containing an zinc ion source or zinc and copper ion sources, and recovering interferon from the culture.

15 Claims, No Drawings

METHOD FOR PRODUCING INTERFERONS

This invention relates to a method for producing interferons.

Interferon (hereinafter sometimes abbreviated as "IFN") is a protein produced by higher animal cells upon induction by viruses or with nucleic acids or mitogens, for example, and has antiviral, antitumor and other activities.

At present, human IFN is known to include three types differing in characteristics, namely α, β and γ types. The α and β types are induced by viruses or with nucleic acids and the γ type is induced by mitogens, among others. Therefore, human IFN has been produced by cultivating human cells or an established cell line but the production has been very small, so that it is impossible to supply human IFN in amounts sufficient for use in a large-scale clinical trial or as a therapeutic agent. However, the recent advances in gene manipulation techniques have made it possible to obtain any of the α, β and γ types in the form of biologically active protein from the culture of Escherichia coli or some other microorganism which carries an expression vector with a structural gene of IFN inserted therein [Nature, 284, 316 (1980); Nature, 287, 411 (1980); Proceedings of the National Academy of Sciences of the United States of America (hereinafter abbreviated to Proc. Nat. Acad. Sci. U.S.A.), 77, 5230 (1980); Nucleic Acids Research, 8, 4057 (1980); Nature, 295, 503 (1982)]. However, such methods cannot be said to be always satisfactory as an industrial method of human IFN production from the viewpoint of the production yield.

Under these circumstances, the present inventors conducted intensive investigations concerning the method of cultivating microorganisms carrying an expression vector with a structural gene of IFN inserted therein, and found that a remarkably high yield of IFN can be attained by conducting the cultivation in a specified chemically defined medium selected in place of the conventional media in which the organic nitrogen source is mostly a natural product. This finding and further studies have now led to completion of the present invention.

Thus, the present invention provides a method for producing interferon which comprises cultivating a microorganism carrying an expression vector with a structural gene of interferon inserted therein in a chemically defined medium containing L-glutamic acid and an iron ion source and recovering interferon from the culture.

For human interferon, three types α, β and γ, are known. In particular, it is known that the α type includes a number of molecular species, and genes such as those coding for interferons A, B, C, D, F, H, I and J have been reported to be cloned and expressed in Escherichia coli (see, e.g. (European Patent Application Publication No. 43980). The expression of the β type IFN gene (see, e.g. European Patent Application Publication No. 48,970) and of the γ type IFN gene (see, e.g. European Patent Application Publication No. 77,670) has also been reported in Escherichia coli. These genes and other human IFN genes capable of expression in a host microorganism may be used in the IFN production according to the invention.

For efficient IFN gene expression in a host microorganism, in particular Escherichia coli, ColEI-derived pBR322 [Gene, 2, 95 (1977)] is most often used as the plasmid for the expression vector. Any other plasmids may also be used, provided that they are replicated and maintained in Escherichia coli. Examples are pBR313 [Gene, 2, 75 (1977)], pBR324, pBR325 [Gene, 4, 121 (1978)], pBR327, pBR328 [Gene, 9, 287 (1980)], pKY2289 [Gene, 3, 1 (1978)], pKY2700 [Seikagaku(Biochemistry) 52, 770 (1980)], pACYC177, pACYC184 [Journal of Bacteriology, 134, 1141 (1978)], pRK248, pRK646 and pDF41 [Methods in Enzymology, 68, 268 (1979)].

Furthermore, bacteriophage-derived vectors, such as λgt·λC of the λgt series derived from λ phage [Proc. Nat. Acad. Sci. U.S.A., 71, 4579 (1974), λgt·λB [Proc. Nat. Acad. Sci. U.S.A., 72, 3416 (1975)], λDam [Gene, 1, 255 (1977)], Charon vectors [Science, 196, 161 (1977); Journal of Virology, 29, 555 (1979)], and filamentous phage-derived vectors may also be used.

The structural gene of IFN is preferably connected downstream from a promoter. Useful promoters include the tryptophan (trp) promoter, lactose (lac) promoter, protein chain elongation factor Tu (tuf B) promoter, rec A promoter, and λP$_L$ and λP$_R$ promoters involved in the growth of λ phage, among others. Any promoter which is functional to promote expression the IFN gene of interest in the desired bacteria may be used.

The construction of the expression vector with a structural gene of IFN inserted therein may be performed by known methods. For α type IFN, for example, the methods described in Nature, 287, 411 (1980), DNA 1, 125 (1982), Nucleic Acids Research, 11, 2927 (1983) and European Patent Application Publication No. 43980, among others, may be mentioned; for β type IFN, the methods described, for example, in Nucleic Acids Research, 8, 4057 (1980), Proc. Nat. Acad. Sci. U.S.A., 77, 5230 (1980), Nucleic Acids Research, 11, 4677 (1983) and European Patent Application Publication No. 48,970 may be mentioned; and for γ type IFN, the methods described, for example, in Nature, 295, 503 (1982), European Patent Application Publication No. 77,670, Japanese Laid-open Patent Application Laid-open No. 189197/1983, Japanese Patent Application No. 176090/1983 (Japanese Laid-open Patent Application Laid-open No. 186995/1984, European Patent Application Publication No. 110,044) and Japanese Patent Application No. 45723/1983 (Japanese Laid-open Patent Application Laid-open No. 169494/1984) may be mentioned, which are hereby incorporated by references.

As the host microorganism into which the expression vector with a structural gene of IFN inserted therein is to be introduced, there is used Escherichia coli. Among others, Escherichia coli K-12-derived strains are particularly preferred from the handling and safety viewpoints. Said Escherichia coli K-12-derived strain include, among others, Escherichia coli strains 294, W3110, C-600, and χ1776. Mutants of these strains may also be used.

As the above strain 294, there may be mentioned the strain described in Proc. Nat. Acad. Sci. U.S.A., 73, 4174 (1976). As the above strain 294, there may also be mentioned the strain listed in The American Type Culture Collection (hereinafter abbreviated as ATCC) Catalogue of Strains I, 15th edition, 1982, under ATCC 31446. As the above strain 294, there may further be mentioned the strain deposited with the Institute for Fermentation, Osaka, Japan under IFO 14171 (European Patent Application Publication No. 89,676).

As the above strain W3110, there may be mentioned the strain listed in the ATCC Catalogue of Strains I, 15th edition, 1982 under ATCC 27325.

As the above strain C-600, there may be mentioned the strain listed in the ATCC Catalogue of Strains I, 15th edition, 1982 under ATCC 23724.

As the above strain $\chi$1776, there may be mentioned the strain described in The Journal of Infectious Diseases, 137, 668 (1978). As the above strain $\chi$1776, there may also be mentioned, for example, in U.S. Pat. No. 4,190,495 and referred to as ATCC 31244 (listed in the ATCC Catalogue of Strains I, 15th edition, 1982).

The introduction of the expression vector (plasmid vector or phage vector) with a structural gene of IFN inserted therein into the host organism may be conducted by conventional methods, such as those described, for example, in Journal of Molecular Biology, 53, 159 (1970), Methods in Enzymology, 68, 253 (1979), and Gene, 3, 279 (1978), which are hereby incorporated by references.

The chemically defined medium to be used in the practice of the invention is a medium all the components of which are known. The media of the present invention comprise a base medium, to which the source of L-glutamic acid and the source of iron ions, as well as other preferred ingredients discussed below, have been added.

As said chemically defined base medium, there may be used those known media mainly composed of inorganic salts, which will support the growth of the bacteria being used, when used in conjunction with a suitable carbon source and oxygenating means. Suitable examples of base media include M-9 medium (see Table 1 below) and Davis medium (see Table 2 below. The TSM-3 medium having the composition of inorganic salts given in Table 3 below may also be used with advantage. In accordance with the present invention, the L-glutamic acid and source of iron ions, as well as other preferred materials discussed below, can be added to to the seed culture medium, and/or to the main culture medium. Preferably it is added to both.

As the seed culture medium, there may be used an ordinary nutrient medium, such as nutrient broth or L-broth. The chemically defined medium (SS-1 medium) given in Table 4 may also be used with advantage.

TABLE 1

| M-9 medium | |
|---|---|
| Na$_2$HPO$_4$ | 6 g/liter |
| KH$_2$PO$_4$ | 3 g/liter |
| NaCl | 0.5 g/liter |
| NH$_4$Cl | 1 g/liter |
| MgSO$_4$.7H$_2$O | 0.34 g/liter |

TABLE 2

| Davis medium | |
|---|---|
| K$_2$HPO$_4$ | 7 g/liter |
| KH$_2$PO$_4$ | 3 g/liter |
| (NH$_4$)$_2$SO$_4$ | 1 g/liter |
| Disodium citrate dihydrate | 0.5 g/liter |

TABLE 3

| TSM-3 medium | |
|---|---|
| KH$_2$PO$_4$ | 1.5 g/liter |
| K$_2$HPO$_4$ | 1.0 g/liter |
| (NH$_4$)$_2$SO$_4$ | 1.25 g/liter |

TABLE 3-continued

| TSM-3 medium | |
|---|---|
| MgSO$_4$.7H$_2$O | 3.5 g/liter |

TABLE 4

| SS-1 medium | |
|---|---|
| Glucose | 5 g/liter |
| (NH$_4$)$_2$SO$_4$ | 5 g/liter |
| KH$_2$PO$_4$ | 1.5 g/liter |
| Na$_2$HPO$_4$.12H$_2$O | 8.4 g/liter |
| NaCl | 5 g/liter |
| MgSO$_4$.6H$_2$O | 3.4 g/liter |
| Sodium L-glutamate | 2 g/liter |
| FeCl$_3$.6H$_2$O | 27 mg/liter |

L-Glutamic acid to be used in accordance with the invention may be in the form of a salt. Said physiologically acceptable such as the sodium salt, potassium salt or ammonium salt. Said L-glutamic acid or a salt thereof is preferably used in an addition level of about 0.1 to 10 g (as L-glutamic acid), more preferably about 1 to 5 g per liter of chemically defined medium.

The iron ion source to be used in the practice of the invention is a substance capable of providing iron ions when dissolved or a substance capable of being utilized in the form of iron ion when dissolved. Examples of said iron ion source are ferrous chloride, ferric chloride, ferrous sulfate, ferric sulfate, ferric phosphate, ferric nitrate, ferric citrate and ferrous lactate. Said iron ion source is added in an amount of about $10^{-5}$ to $10^{-3}$ mole (as iron ion), more preferably about $5 \times 10^{31}$ $^5$ to $5 \times 10^{-4}$ mole per liter of chemically defined medium.

It is advantageous to add, in accordance with a further aspect of the invention, a zinc ion source, a copper ion source, or a zinc ion source plus copper ion source to the chemically defined medium, since the yield of the desired product may sometimes be increased thereby.

The above zinc ion source is a substance capable of providing zinc ions when dissolved or a substance utilizable in the form of zinc ion when dissolved. Examples of said zinc ion source are zinc chloride, basic zinc carbonate, zinc nitrate, zinc sulfate and zinc phosphate. Said zinc ion source is used at an addition level of about $10^{-5}$ to $10^{-3}$ mole (as zinc ion) more preferably about $2 \times 10^{-5}$ to $1 \times 10^{-4}$ mole per liter of chemically defined medium.

The above copper ion source is a substance capable of providing copper ions when dissolved or a substance utilizable in the form of copper ion when dissolved. Examples of said copper ion source are copper sulfate, cupric chloride, cuprous chloride, copper carbonate and copper acetate. Said copper ion source is added in an amount of about $10^{-5}$ to $10^{-3}$ mole (as copper ion), more preferably about $2 \times 10^{-5}$ to $1 \times 10^{-4}$ mole per liter of chemically defined medium.

When the host microorganism is an amino acid-auxotroph, it is necessary to appropriately add the amino acid or amino acids which are required (e.g., L-lysine, L-arginine, L-methionine, L-leucine, L-proline, L-isoleucine, L-valine, L-tryptophan) each in an amount of about 10 to 1000 mg/liter. Vitamins (e.g. calcium pantothenate, choline chloride, folic acid, i-inositol, nicotinamide, pyridoxal hydrochloride, riboflavin, vitamin B$_1$) are not essential unless a vitamin-requiring mutant is used. Nevertheless, the addition of about 1 to 100 mg/liter of vitamin B$_1$ tends to stabilize the fermentation process and therefore an appropriate addition thereof is desired. When the host organism requires a vitamin or vitamins, the required vitamin or vitamins may be added each in an amount of about 1 to 100 mg/liter.

When host microorganism requires nucleic acid-related compounds or other compounds, the required compounds may be added to the culture medium each in an amount of about 1 to 100 mg/liter.

As regards the carbon source to be added to the medium, it is advantageous to maintain its concentration in the range of about 0.1 to 5% (w/v) over the whole incubation period, since this measure causes accumulation of the desired IFN in a significant amount. As said carbon source, there may be mentioned glucose, glycerol, maltose and sorbitol, for example.

The plasmid with a stractural gene coding for an interferon inserted therein generally carries a selection marker, which may comprise a gene which confers resistance to a particular antibiotics. In such case, the addition of that antibiotic (e.g. tetracycline, ampicillin) to the medium is advantageous, since plasmid-bearing strains alone can grow in that instance.

The cultivation is generally carried out in a stirred, oxygenated culture. To conduct the cultivation while maintaining the oxygen concentration in the medium at a level not lower than about 5% (v/v) of the saturation concentration of dissolved oxygen is advantageous, since, in that case, the yield of the desired IFN is increased. For that purpose, it is also effective to supply a mixture of air and/or pure oxygen in the course of cultivation.

In performing the cultivation in accordance with the invention, it is preferable to adjust the pH of the medium generally to about 5 to 7.5. The cultivation temperature is about 15° to 45° C., preferably about 20° to 42° C. It is advantageous to increase the yield of the desired IFN that the cultivation is carried out initially at a temperature of 37° C.±5° C. and then the temperature is reduced stepwise or linearly to a final temperature about 23° C.±5° C. as the cell grows. More preferably, the initial temperature is 37° C.±2° C.; further, the temperature is reduced to 33° C.±2° C. when the cell grows to 20 to 40% of the maximal growth; moreover, it is reduced to 29° C.±2° C. when the cell grows to 40 to 60% of the maximal growth; and then it is reduced to 25° C.±2° C. when the cell grows to 60 to 75% of the maximal growth and the cultivation is continued to give a sufficient amount of the desired IFN or it is reduced to 20° C.±2° C. when the cell grows to 75 to 90% of the maximal growth and the cultivation is continued to give a sufficient amount of the desired IFN. The cultivation period is about 3 to 72 hours.

In the fermentation process according to the invention, IFN is generally accumulated within the microbial cells. For recovering the IFN so accumulated in the culture, therefore, the cells are first harvested by centrifugation or filtration and the IFN is extracted therefrom. For efficient IFN extraction, ultrasonic treatment, treatment with lysozyme, or treatment with a chemical, such as a surfactant, for example, is conducted.

The thus-extracted IFN is purified by the conventional purification method applicable to proteins or peptides, such as salting out with ammonium sulfate, precipitation with alcohol, ion exchange chromatography, cellulose column chromatography and/or gel filtration. Especially when such methods are combined with monoclonal antibody separation techniques, such as affinity chromatography utilizing monoclonal antibodies directed to the IFN of choice, very high purity products can be obtained.

Thus, for example, an extract from the culture is centrifuged, the supernatant is applied, for example, to a monoclonal antibody column, the column is washed, and then elution is conducted, for example, with 0.2 M acetic acid, 0.1% Triton X100 (polyoxyethyleneglycol-p-t-octhyphenyl ether) and 0.15 M NaCl. In this procedure, interferon is specifically adsorbed on the monoclonal antibody column, so that a high purity sample can be obtained with ease. [For the purification of $\alpha$ type IFN, see Scientific American, 243, (4), 56 (1980); for the purification of $\gamma$ type IFN, see Japanese Patent Application No. 176091/1983, European Patent Application Publication No. 103,898)].

Using such techniques on the IFN's produced in accordance with the present invention, human leukocyte IFN$\alpha$A protein, for example, can be purified to a specific activity of not less than $10^8$ U/mg when subjected to antiviral activity measurement by the test for inhibition of the cytopathic effect of vesicular stomatitis virus (VSV) on bovine kidney-derived MDBK cells, and human immune IFN protein obtained can be purified to a specific activity of not less than $10^7$ U/mg when subjected to antiviral activity measurement by the test for inhibition of the cytopathic effect of vesicular stomatitis virus (VSV) on human amnion-derived WISH cells [cf. Japanese Patent Application No. 176091/1983 (European Patent Application Publication No. 103,898)].

The human IFN proteins produced in accordance with the invention are equal in physicochemical and biological properties to those obtained by cultivating the same transformants in conventional nutrient medium.

Therefore, the IFN produced by the method of the invention can be used for the same purposes and in the same manner as the IFN produced by conventional methods.

IFN has antiviral, antitumor, antiproliferative, immunopotentiating and other activities and therefore can be used in the treatment of viral infections, tumors and so on in mammals (e.g. human, cattle, horse, swine, mouse, rat). In using IFN as an antiviral, antitumor, antiproliferative or immunopotentiating agent, for example, IFN is mixed, for example, with a per se known, pharmacologically acceptable carrier, excipient or diluent and thus administered parenterally, as an injection by intravenous or intramuscular injection or by some other route. The daily dose is about 100 thousand to 100 million units, preferably about 1 million to 50 million units, per normal human individual. In mammals other than human, the dose is 2000 to 2 million units/kg/day, preferably about 20 thousand to 1 million units/kg/day.

The following test examples and working examples are further illustrative of the present invention.

EXAMPLE 1

Glucose was added as a carbon source in an amount of 10 g/liter to the above-mentioned M-9 medium or TSM-3 medium. This medium, with or without addition of sodium glutamate, was inoculated with *Escherichia coli* 294 (ATCC 31446)/pLe IF A trp 25 (European Patent Application Publication No. 43980, which is hereby incorporated by reference), followed by incubation at 37° C. for 16 hours. The growth of the strain was examined and the results are shown in Table 5.

TABLE 5

Effects of Sodium L-glutamate on bacterial growth

| Medium | Bacterial growth (Klett units/ml) Sodium glutamate | | |
|---|---|---|---|
| | 0 | 1 g/liter | 4 g/liter |
| M-9 medium | 30 | 280 | 340 |
| TSM-3 medium | 35 | 280 | 330 |

EXAMPLE 2

A 5-liter jar fermenter was charged with 2.5 liter of a medium prepared by adding 25 g/liter of glucose and 4 g/liter of sodium L-glutamate to TSM-3 medium. The metal salts given in Table 6 were added thereto. The resulting medium was inoculated with 50 ml of a seed culture of *Escherichia coli* 294 (ATCC 31446)/pLe IF A trp 25 carrying a plasmid with the structural gene of human leukocyte IFN-αA inserted therein, followed by cultivation at 37° C. with agitation at a rate of 1000 rpm and aeration at a rate of 2.5 liters/minute. During the cultivation, the temperature was lowered stepwise from 37° C. to 33° C., 29° C. and 25° C., for example, with the bacterial growth. Furthermore, new 2.5% portions of glucose were added when the glucose concentration became lower than 1% in the course of cultivation. The cultivation was continued for 27 hours. The pH was maintained at 6.8 with aqueous ammonia throughout the cultivation period. The bactrial growth and the yield of human leukocyte interferon αA were examined and the results as shown in Table 6 were obtained.

TABLE 6

Effects of trace metal salts on bacterial growth and IFN production

| $FeCl_3.6H_2O$ (mg/l) | $CuSO_4.5H_2O$ (mg/l) | $ZnSO_4.7H_2O$ (mg/l) | Growth* | Productivity of human leukocyte interferon αA** |
|---|---|---|---|---|
| 27 | 8 | 8 | 100 | 100 |
| 27 | 0 | 8 | 88 | 75 |
| 27 | 8 | 0 | 76 | 52 |
| 27 | 0 | 0 | 75 | 35 |
| 0 | 8 | 0 | 17 | 9 |
| 0 | 0 | 8 | 10 | 5 |
| 0 | 0 | 0 | 26 | 7 |

Notes:
*The bacterial turbidity was measured with a Klett-Summerson colorimeter and the extent of growth was expressed in terms of relative value taking the extent of growth in the case in which iron, copper and zinc ions were added as 100.
**The accumulation of IFN was measured in terms of antiviral activity and expressed in terms of relative value taking the yield in the case in which iron, copper and zinc ions were added as 100.

EXAMPLE 3

Seed cultures were prepared by charging 200 ml Erlenmeyer flasks with 50 ml of (A) conventional nutrient medium (L-broth) described in Table 7 and (B) the SS-1 medium containing the sources of L-glutamate and iron ions, as discussed in Table 4, above. Following addition of 5 mg/liter of tetracycline hydrochloride, the medium was inoculated with *Escherichia coli* 294 (ATCC 31446)/pLe IF A trp 25 carrying a plasmid with the structural gene of human leukocyte IFN-αA inserted therein and then incubation was conducted at 37° C. for 12 or 16 hours.

TABLE 7

| Seed culture medium (L-broth) | |
|---|---|
| Bacto Trypton (Difco, USA) | 10 g/liter |
| Bacto Yeast extract (Difco, USA) | 5 g/liter |
| Sodium chloride | 5 g/liter |

Then, to the above-mentioned TSM-3 medium, there were added 25 g/liter of glucose, 4 g/liter of sodium -L-glutamate, 27 mg/liter of $FeCl_3.6H_2O$, 8 mg/liter of $CuSO_4.5H_2O$, 8 mg/liter of $ZnSO_4.7H_2O$, 70 mg/liter of thiamine hydrochloride and 5 mg/liter of tetracycline hydrochloride. 5-Liter jar fermenters were charged with 2.5 liters of the resulting medium. Following inoculation with the above seed cultures (A) and (B), cultivation was carried out under the same conditions as used in Test Example 2, and the bacterial growth and the yield of human leukocyte IFN were examined. The results obtained are shown in Table 8.

TABLE 8

Effects of seed culture on IFN production

| Seed culture medium | Fermentation period (hrs.) | Growth* | Productivity of human leukocyte interferon αA** |
|---|---|---|---|
| L-broth-medium | 18 | 100 | 100 |
| | 24 | 155 | 420 |
| SS-1 seed medium | 18 | 160 | 390 |
| | 24 | 190 | 620 |

Notes:
*The bacterial turbidity was measured using a Klett-Summerson colorimeter and the extent of growth was expressed in terms of relative value taking the extent of growth in the case in which L-broth medium was used and incubation was conducted for 18 hours as 100.
**The accumulation of IFN was measured in terms of antiviral activity and expressed in terms of relative value taking the yield in the case in which L-broth medium was used and incubation was conducted for 18 hours as 100.

As is evident from Table 8, the use of the seed culture in the chemically defined medium (SS-1 seed medium) results in increased bacterial growth in fermentation and in increased IFN production as compared with the use of the seed culture prepared in the non-augmented nutrient medium (L-broth medium).

EXAMPLE 4

A 200-ml Erlenmeyer flask was charged with 50 ml of SS-1 seed medium. Following addition of 5 mg/liter of tetracycline hydrochloride, the medium was inoculated with *Escherichia coli* 294 (ATCC 31446)/pLe IF A trp 25 carrying a plasmid with the structural gene of human leukocyte IFN-αA inserted therein. Cultivation was conducted at 37° C. for 16 hours. Then, to TSM-3 medium, there were added 4 g/liter of sodium L-glutamate, 27 mg/liter of ferric chloride, 8 mg/liter of copper sulfate, 8 mg/liter of zinc sulfate, 70 mg/liter of thiamine hydrochloride and 5 mg/liter of tetracycline hydrochloride. A 5-liter jar fermenter was charged with 2.5 liters of the resulting medium. Glucose was added thereto in the manner given in Table 9. Following inoculation with the above seed culture, cultivation was started at an aeration rate of 2.5 liters/minute, an agitation rate of 1000 rpm and a temperature of 37° C. With the growth of bacteria, the cultivation temperature was lowered stepwise from 37° C. to 33° C., 29° C. and 25° C. to thereby maintain the dissolved oxygen concentration at a level not lower than 10% of the saturation oxygen concentration. During the cultivation, the pH was adjusted to 6.8 with aqueous ammonia. Cultivation was continued for 27 hours. The bacterial growth and the yield of human leukocyte IFN-αA were examined. The results thus obtained are shown in Table 9.

TABLE 9

Effects of glucose concentration

| Run No. | Initial glucose concentration (w/v) | Addition of glucose during cultivation | Growth* | Productivity of IFN-αA** |
|---|---|---|---|---|
| 4-1 | 1% | 1% × 9 times | 100 | 100 |
| 4-2 | 2.5% | 2.5% × 3 times | 99 | 94 |
| 4-3 | 5.0% | 5% × 1 time | 89 | 83 |
| 4-4 | 7.5% | 2.5% × 1 time | 59 | 22 |
| 4-5 | 10% | 0 | 16 | 4 |

*The bacterial turbidity was measured with a Klett-Summerson colorimeter and expressed in relative value taking the growth in Run No. 4-1 as 100.
**The accumulation of IFN was measured in terms of antiviral activity and expressed in relative value taking the productivity in Run No. 4-1 as 100.

From Table 9, it is evident that the bacterial growth and IFN-αA production are markedly increased under the conditions of Run Nos. 4-1, 4-2 and 4-3.

EXAMPLE 5

A 5-liter jar fermenter containing 2.5 liters of (1) a medium (nutrient medium) prepared by adding 25 g/liter of glucose, 5 g/liter of Casamino acid (Difco, U.S.A.), 70 mg/liter of vitamin $B_1$ hydrochloride and 5 mg/liter of tetracycline hydrochloride to M-9 medium or (2) a medium (chemically defined medium) prepared by adding 25 g/liter of glucose, 4 g/liter of sodium L-glutamate, 27 mg/liter of $FeCl_3.6H_2O$, 8 mg/liter of $CuSO_4. 5H_2O$, 8 mg/liter of $ZnSO_4.7H_2O$, 70, mg/liter of vitamin $B_1$ hydrochloride, 5 mg/liter of tetracycline hydrochloride, 50 mg/liter of L-proline and 50 mg/liter of L-leucine to M-9 medium was inoculated with *Escherichia coli* 294 (ATCC 31446)/pLe IF A trp 25 carrying a plasmid with the structural gene of human leukocyte IFN-αA inserted therein (European Patent Application Publication No. 43,980, which is hereby incorporated by reference). Cultivation was started at an aeration rate of 2.5 liters/minute, an agitation rate of 1000 rpm and a temperature of 37° C. In the course of cultivation, the temperature was lowered to 33° C. at OD 3000 KU, to 29° C. at OD 5000 KU and to 25° C. at OD 7000 KU. In this manner, the cultivation was continued for 48 hours. The dissolved oxygen concentration was maintained at not less than 5% during the cultivation. When, during cultivation, the glucose concentration lowered to 1% or below, glucose was added at a rate of 25 g/liter. The results thus obtained are shown in Table 10.

TABLE 10

| Medium | Productivity of human leukocyte IFN* |
|---|---|
| (1) Nutrient medium | 100 |
| (2) Chemically defined medium | 520 |

*The accumulation of IFN was measured in terms of antiviral activity and expressed in terms of relative value taking the productivity in the case in which the nutrient medium was used as 100.

As is evident from the above table 10, the addition, to the chemically defined medium (2), of various compounds according to invention resulted in a remarkable increase in IFN productivity.

Cells were harvested by centrifugation of 2 liters of the culture broth in chemically defined medium (2). The cells were suspended in 100 ml of 50 mM Tris-HCl (pH 7.6) containing 10% sucrose, 0.2 M NaCl, 10 mM ethylenediaminetetraacetate (EDTA), 10 mM spermidine, 2 mM phenylmethylsulfonyl fluoride (PMSF) and 0.2 mg/ml lysozyme. The suspension was stirred at 4° C. for an hour, then maintained at 37° C. for 5 minutes, and treated in a sonicator (Altec, USA) at 0° C. for 40 seconds. The lysate was centrifuged at 11,300×g for an hour to give 95 ml of a supernatant.

This supernatant (95 ml) was diluted to 300 ml with 20 mM Tris-HCl (pH 7.6) containing 1 mM EDTA and 0.15 M NaCl (TEN) and the diluted solution was applied to an anti-IFN-αA antibody column (20 ml).

After washing the column well with TEN, elution was performed with 0.2 M acetic acid containing 0.1% Tween 20 (Wako Pure Chemical Industries, Japan). Active fractions ere combined, adjusted to pH 4.5 and applied to a CM cellulose column for adsorption. The column was washed well and elution was conducted with 0.025 M ammonium acetate buffer (pH 5.0) containing 0.15 M NaCl. Again, active fractions were combined and lyophilized to give 320 mg of a human leukocyte IFN-αA powder.

SDS-polyacrylamide gel electrophoresis revealed that this product had a molecular weight of 19000±1000. The antiviral activity of the human leukocyte IFN protein finally obtained here was $2×10^8$ U/mg. With respect to other physico-chemical properties, amino acid composition and peptide mapping, the product behaved in quite the same manner as recombinant human leukocyte IFN produced in conventional medium.

EXAMPLE 6

A 5-liter fermenter containing 2.5 liters of (1) a medium (nutrient medium) prepared by adding, to TSM-3 medium, 25 g/liter of glucose, 20 g/liter of yeast extract and 5 mg/liter of tetracycline hydrochloride or (2) a medium (chemically defined medium) prepared by adding, to TSM-3 medium, 25 g/liter of glucose, 4 g/liter of sodium L-glutamate, 27 mg/liter of $FeCl_{13}. 6H_2O$, 8 mg/liter of $CuSO_4. 5H_2O$, 8 mg/liter of $ZnSO_4. 7H_2O$, 70 mg/liter of thiamine hydrochloride and 5 mg/liter of tetracycline hydrochloride was inoculated with *Escherichia coli* 294 (IFO 14171)/pHIT. trp 2101 [Japanese Patent Application No. 176090/1983 (Japanese Patent Application Laid-open No. 186995/1984, European Patent Application Publication No. 110,044), which are incorporated by reference.] carrying an expression plasmid with the structural gene of human immune IFN inserted therein. Cultivation was started at an aeration rate of 2.5 liters/minute, a stirring rate of 1000 rpm and a temperature of 37° C. In the course of cultivation, the temperature was lowered to 33° C. when the OD reached 2000 Klett units, to 29° C. when the OD reached 4000 Klett units and to 25° C. when the OD attained 6000 Klett units. In this manner, the cultivation was continued for 26 hours. The pH of the culture medium was maintained at 6.8 with aqueous ammonia. In the course of cultivation, 25 g/liter of glucose was added each time when the glucose concentration in the medium became lower than 1%. As a result, the productivity in chemically defined medium (2) was 550 when the IFN-γ productivity in nutrient medium (1) was taken as 100.

Bacterial cells were harvested by centrifuging 2.4 liters of the chemically defined medium culture as obtained above and suspended in 120 ml of 50 mM Tris-HCl (pH 7.6) containing 10% sucrose, 10 mM EDTA, 10 mM spermidine, 2 mM PMSF and 0.2 mg/ml lysozyme. The suspension was stirred at 4° C. for an hour, then maintained at 37° C. for 5 minutes, and treated on a sonicator (Altec, USA). The lysate was centrifuged at $11,300 \times g$ for an hour to give 115 ml of a supernatant.

The supernatant (115 ml) was diluted to 360 ml with TEN and the diluted solution was applied to an anti-IFN-γ antibody column (25 ml) [cf. Examples 12 and 13 of Japanese Patent Application No. 176091/1983 (European Patent Application Publication No. 103,898), which are incorporated by reference.] After washing the column well with TEN, the column was further washed with 20 mM Tris-HCl (pH 7.0) containing 1 M NaCl and 0.1% Tween 20, followed by elution with Tris-HCl (pH 7.0) containing 2 M guanidine hydrochloride (Sigma, USA). The thus-obtained active fractions (100 ml) were dialyzed against a buffer containing 0.115% $Na_2HPO_4$, 0.02% $KH_2PO_4$, 0.8% NaCl and 0.02% KCl at 4° C. for 18 hours.

The human immune IFN protein finally obtained in this manner weighed 47 mg and had an antiviral activity of $2 \times 10^7$ U/mg.

The molecular weight of the samples obtained herein as determined by SDS-polyacrylamide electrophoresis was $18000 \pm 1000$. With respect to other physico-chemical properties, amino acid composition and peptide mapping, the sample behaved in quite the same manner as recombinant human immune IFN produced in conventional medium.

What we claim is:

1. A method for producing interferon which comprises cultivating an *E. coli* carrying an expression vector with a structural gene of interferon inserted therein in a chemically defined medium containing L-glutamic acid in a concentration of about 0.1 to about 10 g/liter and an iron ion source in a concentration of about $10^{-5}$ to about $10^{-3}$ mole/liter and recovering interferon from the culture.

2. A method as claimed in claim 1, wherein the medium further contains a zinc ion source.

3. A method as claimed in claim 1, wherein the medium further contains a copper ion source.

4. A method as claimed in claim 2, wherein the medium further contains a copper ion source.

5. A method as claimed in claim 1, wherein the structural gene of interferon is the structural gene of human leukocyte interferon.

6. A method as claimed in claim 1, wherein the structural gene of interferon is the structural gene of human immune interferon.

7. A method as claimed in claim 2, wherein the medium contains the zinc ion source in a concentration of about $10^{-5}$ to $10^{-3}$ mole/liter.

8. A method as claimed in claim 3, wherein the medium contains the copper ion source in a concentration of about $10^{-5}$ to $10^{-3}$ mole/liter.

9. A method as claimed in claim 4, wherein the medium contains the copper ion source in a concentration of about $10^{-5}$ to $10^{-3}$ mole/liter and the zinc ion source is in a concentration of about $10^{-5}$ to $10^{-3}$ mole/liter.

10. A method as claimed in claim 1, wherein the medium further comprises a carbon source, and the cultivation is conducted while maintaining the carbon source concentration in the medium at about 0.1 to 5%.

11. A method as claimed in claim 10, wherein the cultivation is conducted while maintaining the oxygen concentration in the medium at a level not lower than about 5% of the saturation concentration of dissolved oxygen.

12. A method as claimed in claim 1, wherein the cultivation is conducted while starting the cultivation at a temperature of 37° C.±5° C. and reducing the temperature as the cell grows to finally 23° C.±5° C.

13. The method of claim 1 wherein the medium contains the iron ion source in a concentration of about $5 \times 10^{-5}$ to about $5 \times 10^{-4}$ moles per liter.

14. The method of claim 1 wherein the medium contains the L-glutamic acid in a concentration of about 1 to about 5 g per liter.

15. The method of claim 9 wherein the medium is TSM-3 medium.

* * * * *